United States Patent [19]

D'Silva

[11] 4,080,469

[45] Mar. 21, 1978

[54] CARBAMATE PESTICIDAL COMPOSITIONS

[75] Inventor: Themistocles D. J. D'Silva, South Charleston, W. Va.

[73] Assignee: Union Carbide Corporation, New York, N.Y.

[21] Appl. No.: 486,632

[22] Filed: Jul. 8, 1974

[51] Int. Cl.² .............................................. A01N 9/00
[52] U.S. Cl. .................................. 424/298; 424/304; 424/327
[58] Field of Search ............... 424/298, 304, 300, 327; 260/453 R

[56] References Cited

U.S. PATENT DOCUMENTS

| | | | |
|---|---|---|---|
| 3,639,633 | 2/1972 | Buchanan | 424/327 |
| 3,726,908 | 4/1973 | Buchanan | 424/298 X |
| 3,812,209 | 5/1974 | Brown | 424/298 X |

Primary Examiner—Leonard Schenkman
Attorney, Agent, or Firm—Robert C. Brown

[57] ABSTRACT

Novel N-Dithioalkyl carbamoyloximines have exceptional pesticidal activity.

36 Claims, No Drawings

CARBAMATE PESTICIDAL COMPOSITIONS

This invention relates to methods and compositions for combatting insects and mites.

The compounds which are employed as the active ingredients in the pesticidal compositions of this invention are new compounds corresponding to the following general formula:

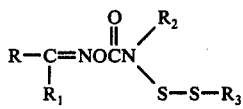

wherein:

R may be carbamoyl, lower alkyl, lower alkylthio or lower alkyl substituted with one or more lower alkoxy, lower alkylthio, lower alkylsulfinyl, lower alkylsulfonyl, phenylthio, phenylsulfinyl, phenylsulfonyl, lower phenylalkylthio, lower phenylalkylsulfinyl, lower phenylalkylsulfonyl, lower alkylcarbamoyl, dilower alkylcarbamoyl or $R_4CON(R_5)$— groups all of which groups may be further substituted with one or more chloro, bromo, fluoro, nitro cyano or amido substituents and the phenyl moieties of said groups may be still further substituted with one or more lower alkyl or lower alkoxy groups.

$R_1$ may be, hydrogen, chloro, bromo, fluoro, cyano or lower alkyl groups having from 1 to 4 carbon atoms or a lower alkylthio, lower alkoxy, lower carboalkoxyalkylthio or lower alkylthioalkyl groups in which any alkyl moiety may be substituted with one or more chloro, bromo, fluoro, cyano, amido or nitro substituents.

$R_2$ may be lower alkyl or lower alkyl substituted with one or more chloro, bromo, fluoro, nitro or cyano substituents or phenyl or lower phenyl alkyl either unsubstituted or substituted with one or more chloro, bromo, fluoro, nitro, cyano, lower alkyl or lower alkoxy substituents.

$R_3$ may be alkyl, alkenyl, cycloalkyl, bicycloalkyl, cycloalkenyl, bicycloalkenyl or phenyl or lower phenyl alkyl either unsubstituted or substituted with one or more chloro, bromo, fluoro, nitro, cyano, lower alkyl, lower alkoxy or lower haloalkyl substituents.

$R_4$ and $R_5$ are individually hydrogen or lower alkyl.

These compositions with varying degrees of efficacy are useful in combating insects and mites. In general, the compositions having the greatest degree of pesticidal activity are those in which the combined total number of aliphatic carbon atoms in the substituents R, $R_1$ and $R_2$ does not exceed about 10 carbon atoms.

The preferred compositions of this invention are those in which both $R_2$ and $R_3$ are lower alkyl.

It will be appreciated that the new compositions of this invention will exist in at least two isomeric forms. In the "syn" configuration, the oxygen atom of the oximino function is on the same side of the oximino double bond as the $R_1$ substituent in the generic formula set forth above while in the "anti" configuration, the oxygen atom is on the opposite side of the oximino function. Both isomers are within the scope of my invention, however, the syn isomers are preferred due to their greater biological activity.

The novel compositions of this invention in comparison to the corresponding N-methylcarbamate compositions, some of which are well known insecticides, have been found to possess essentially equivalent insecticidal and miticidal activity although in some cases enhanced activity against particular pests have been observed. Surprisingly, however, the compositions of this invention demonstrate a sharp reduction in mammalian toxicity as compared to the N-methyl compounds and a dramatic reduction in phytotoxicity to important economic crops such as cotton, tomatoes, beans and corn which are highly susceptible to phytotoxic injury by certain of the corresponding N-methyl carbamate compositions such as methomyl. In addition nearly all of the novel compositions of this invention are quite stable under normal conditions and can be stored for long periods of time without appreciable loss or reduction in biological activity. This is to be contrasted with many of the corresponding N-methyl carbamate compositions which are relatively unstable and can not be stored for any appreciable length of time and as such are not useful pesticides because of practical considerations.

The new compositions of this invention can be prepared conveniently in accordance with the following general reaction scheme:

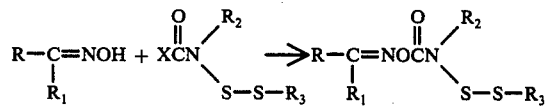

where R, $R_1$, $R_2$ and $R_3$ are as described above and where X is either chlorine or fluorine.

The oximine precursors used in the preparation of a novel compositions of this invention can be prepared by conventional means as for example by the methods described in U.S. Pat. Nos. 3,217,036, 3,217,037, 3,400,153, 3,536,760 and 3,576,834.

The carbamic acid halide compositions used in the preparation of the novel compositions of this invention can be prepared by reacting an appropriately substituted thiosulfenyl chloride with an appropriately substituted carbamoyl fluoride; by the reaction of an appropriately substituted N-chlorothio carbamoyl chloride with an appropriately substituted mercaptan or by the reaction between a substituted thiosulfenylamino compound and phosgene all of which are described in more detail in my copending U.S. patent application Ser. No. 486,631 filed concurrently herewith.

The reaction between the oxime compound and the carbamic acid halide composition is preferably carried out in an aprotic solvent and in the presence of a base. The preferred base materials are tertiary amines and alkaline earth bases. Yields obtained by this reaction are generally quantitative.

The following specific examples are presented to more particularly illustrate the manner in which the new compounds of this invention may be prepared.

EXAMPLE I

Preparation of N-Methyl-N(2-Methyl-2-Propanethio Sulfenyl)-Carbamoyl Fluoride

To a solution of 231.08 N-methylcarbamoyl fluoride, in 600 ml toluene, cooled to 0° C was added 478.0 g 2-methyl-2-propanethiosulfenyl chloride dissolved in 1000 ml toluene. This was followed by dropwise addition of 303.0 g triethylamine in 1000 ml of toluene. Stirring was continued for an additional 2 hr. at 5° C. The precipitated salt was filtered off the filtrate concentrated. Wt. of reddish oil 577.0 g. b.p. 75°–80° C/0.5

Torr. $N_D^{22}$ 1.4983. IR(Neat) 5.6 (C=O), 6.9, 7.7, 8.65, 9.25, 9.4 (sh), 10.62 and 13.4 μ NMR(CDCl₃) δ 1.4, (S), 9H, t-Bu; 3.23 (d), J=1.0Hz, 3H, CH₃N.

EXAMPLE II

Preparation of Methylthioacetaldehyde-O-[N-methyl-N-2(2-methyl-propanethiosulfenyl)carbamoyl]oxime.

To a solution of 2.83 g (0.027 m) 1-methylthioacetaldoxime and 11.15 g (0.027 m) N-methyl-N-2(2-methyl-propanethiosulfenyl)carbamoyl fluoride in 75 ml dioxane, was added dropwise 2.72 g (0.027 m) triethylamine. After stirring for 72 hrs. at ambient temperature, the reaction mixture was concentrated under reduced pressure, diluted with water and extracted with ethylacetate. The organic extract was washed with water, dried over magnesium sulfate and concentrated. Crystallized from isopropylether-hexane solution. m.p. 67°–69° C.

Calc'd. for C₉H₁₈N₂O₂S₃: C, 38.46; H, 6.40; N, 9.88. Found: C, 38.57; H, 6.20, N, 9.95.

EXAMPLE III

Preparation of 1-Isopropylthioacetaldehyde-O-[N-methyl-N-2-(2-methylpropanethiosulfenyl)carbamoyl]oxime.

To a solution of 2.08 g isopropylthioacetaldoxime and 6.69 g of a 50% solution of N-methyl-N-2-(2-methyl-propanethiosulfenyl)carbamoyl fluoride in 50 ml dioxane was added dropwise 1.58 g triethylamine. After stirring at room temperature for 20 hrs. the salt was filtered off and the filtrate concentrated under vacuo. The product was taken in ethylacetate, washed with water, dried and concentrated to an oil.

Cald'd. for C₁₁H₂₂N₂O₂S₃: C, 42.55; H, 7.14; N, 9.02. Found: C, 43.33; H, 7.06; N, 8.49.

The following compositions in addition to those described in the above examples are illustrative of the new compounds of this invention:

1-Methylthioacetaldehyde-O-[N-methyl-N-methylthiosulfenylcarbamoyl]oxime
1-Methylthioacetaldehyde-O-[N-methyl-N-2-propanethiosulfenyl)carbamoyl]oxime
1-Isopropylthioacetaldehyde-O-[N-methyl-N-butanethiosulfenylcarbamoyl]oxime
1-(2-cyanoethylthio)acetaldehyde-O-[N-methyl-N-octadecanethiosulfenylcarbamoyl]oxime
1-(3-nitroethylthio)propionaldehyde-O-[N-methyl-N-(2-(2-methylpropane)thiosulfenyl)carbamoyl]oxime
1-(methylthioethylthio)acetaldehyde-O-[N-methyl-N-methylthiosulfenylcarbamoyl]oxime
1-Methylthioacetaldehyde-O-[N-methyl-N-(4-chlorophenylthiosulfenyl)carbamoyl]oxime
1-Methylthioacetaldehyde-O-[N-methyl-N-(4-nitrophenylthiosulfenyl)carbamoyl]oxime
1-Methylthioacetaldehyde-O-[N-methyl-N-(3-trifluoromethylphenylthiosulfenyl)carbamoyl]oxime
1-Methylthioacetaldehyde-O-[N-methyl-N-(4-methylphenylthiosulfenyl)carbamoyl]oxime
1-Methylthioacetaldehyde-O-[N-methyl-N-(3,4-dimethylphenylthiosulfenyl)carbamoyl]oxime
1-[Ethoxycarbamoylmethylthio]acetaldehyde-O-[N-methyl-N-(4-chlorophenylthiosulfenyl)carbamoyl]oxime
1-[N-methylacetamidomethylthio]acetaldehyde-O-[N-methyl-N-2(2-methylpropanethiosulfenyl)carbamoyl]oxime
1-Methylthioacetaldehyde-O-[N-phenyl-N-methanethiosulfenylcarbamoyl]oxime
1-Methylthioacetaldehyde-O-[N-chloroethyl-N-methanethiosulfenylcarbamoyl]oxime
1-Methylthioacetaldehyde-O-[N-p-chlorophenyl-N-propanethiosulfenylcarbamoyl]oxime
1-Methylthioacetaldehyde-O-[N-methyl-N-(2-(2-methylpropane)thiosulfenyl)carbamoyl]oxime
1-(2-propylthio)acetaldehyde-O-[N-methyl-N-(2-(2-methylpropane)thiosulfenyl)carbamoyl]oxime
1-(2-cyanoethylthio)acetaldehyde-O-[N-methyl-N-(2-(2-methylpropane)thiosulfenyl)carbamoyl]oxime
1-Methylthioacetaldehyde-O-[N-methyl-N-(4-t-butylphenylthiosulfenyl)carbamoyl]oxime
1-Methylthioacetaldehyde-O-[N-methyl-N-(2-(2-methylpropane)thiosulfenyl)carbamoyl]oxime
2-Methyl-2-nitropropionaldehyde-O-[N-methyl-N-(2-(2-methylpropane)thiosulfenyl)carbamoyl]oxime
3-Methyl-3-nitrobutanone-2-O-[N-methyl-N-ethanethiosulfenylcarbamoyl]oxime
2-Methyl-2-cyanopropionaldehyde-O-[N-methyl-N-methanethiosulfenylcarbamoyl]oxime
2-Methyl-2-cyanopropionaldehyde-O-[N-methyl-N-octylthiosulfenylcarbamoyl]oxime
2-Methyl-2-cyanopropionaldehyde-O-[N-methyl-N-(2(2-methylpropane)thiosulfenyl)carbamoyl]oxime
2-Methyl-2-nitropropionaldehyde-O-[N-methyl-N-(4-t-butylphenylthiosulfenyl)carbamoyl]oxime
2-Methyl-2-formamidopropionaldehyde-O-[N-methyl-N-butanethiosulfenylcarbamoyl]oxime
2-Methyl-2-acetamidopropionaldehyde-O-[N-methyl-N-(2-(2-methylpropane)thiosulfenyl)carbamoyl]oxime
3-Methyl-3-acetamidobutanone-2-O-[N-methyl-N-octylthiosulfenylcarbamoyl]oxime
2-Methyl-2-methoxypropionaldehyde-O-[N-methyl-N-dodecylthiosulfenylcarbamoyl]oxime
2-Methyl-2-(1-ethoxycarbonylethylthio)propionaldehyde-O-[N-methyl-N-methanesulfenylcarbamoyl]oxime
2-Methyl-2-methylthiopropionaldehyde-O-[N-methyl-N-(2-(2-methylpropane)thiosulfenyl)carbamoyl]oxime
2-Methyl-2-methylsulfinylpropionaldehyde-O-[N-methyl-N-octylthiosulfenylcarbamoyl]oxime
2-Methyl-2-methylthiopropionaldehyde-O-[N-methyl-N-(4-t-butylphenylthiosulfenyl)carbamoyl]oxime
2-Methyl-2-methylthiopropionaldehyde-O-[N-methyl-N-(4-chlorophenylthiosulfenyl)carbamoyl]oxime
2-Methyl-2-(4-chlorophenylthio)propionaldehyde-O-[N-methyl-N-methanethiosulfenyl carbamoyl]oxime
3,3-Dimethyl-1-methylthiobutanone-2-O-[N-methyl-N-methanethiosulfenylcarbamoyl]oxime
3,3-Dimethyl-1-methylthiobutanone-2-O-[N-methyl-N-(2-(2-methylpropane)thiosulfenyl)carbamoyl]oxime
1,2,2-Tris-(methylthio)propionaldehyde-O-[N-methyl-N-methanethiosulfenylcarbamoyl]oxime
2-Methyl-1,2-bis(methylthio)propionaldehyde-O-[N-methyl-N-octanethiosulfenylcarbamoyl]oxime
2-Methyl-2-methoxy-1-chloropropionaldehyde-O-[N-methyl-N-(2(2-methylpropane)thiosulfenyl)carbamoyl]oxime
2-Methyl-1-2-dicyanopropionaldehyde-O-[N-methyl-N-(2(2-methylpropane)thiosulfenyl)carbamoyl]oxime
2-Methyl-2-cyano-1-methylthiopropionaldehyde-O-[N-methyl-N-octadicanethiosulfenylcarbamoyl]oxime 2-Methyl-2-cyano-1-(2-cyanoethylthio)propionaldehyde-O-[N-methyl-N-methanethiosulfenylcarbamoyl]oxime 2-Methyl-2-nitro-1-(2-cyanoethylthio)propionaldehyde-O-[N-methyl-N-(2(2-methylpropane)thiosulfenyl)carbamoyl]oxime 2-(Methylthiomethyl)-2-methylthiopropionaldehyde-O-[N-methyl-N-(2-(2-methylpropane)thiosulfenyl)carbamoyl]oxime 2-(Ethoxymethyl)-2-methylthiopropionaldehyde-O-[N-methyl-N-butanethiosulfenylcarbamoyl]oxime 2-Methyl-2-methylsulfonylpropionaldehyde-O-[N-methyl-N-methanethiosulfenylcarbamoyl]oxime Methylthiochloroformaldehyde-O-[N-methyl-N-(2(2-methylpropane)thiosulfenyl)carbamoyl]oxime 2-Cyanoethylthiochloroformaldehyde-O-[N-methyl-N-methylthiosulfenyl carbamoyl]oxime Bis-methylthioformaldehyde-O-[N-methyl-N-(2-(2-methylpropane)thiosulfenyl)carbamoyl]oxime (Benzylthio)methylthioformaldehyde-O-[N-methyl-N-pentanetriosulfenylcarbamoyl]oxime (Methoxy)methylthioformaldehyde-O-[N-methyl-N-octanethiosulfenylcarbamoyl]oxime Allylthiochloroformaldehyde-O-[N-methyl-N-methanethiosulfenylcarbamoyl]oxime Bis-methylthioformaldehyde-O-[N-methyl-N-(3-trifluoromethylphenylthiosulfenyl)carbamoyl]oxime Bis-methylthioformaldehyde-O-[N-methyl-N-cyclohexanethiosulfenylcarbamoyl]oxime (2-cyanoethylthio)methylthioformaldehyde-O-[N-methyl-N-butanethiosulfenylcarbamoyl]oxime Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which has been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on thier sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introdued into each dish and the dishes were closed. The closed dishes were labeled and held at 80°–85° F. for 3 days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica,* L.) reared according to the specifications of the Chemical Specialities Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table I below. In these tests the pesticidal activity of the compounds against aphid, mite, Southern Armyworm, Bean Beetle and house fly was rated as follows:

C = no control
B = partial control
A = excellent control

Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I

BIOLOGICAL DATA

| Structure | m.p. °C | Aphid | Mite | Armyworm | Beetle | Fly | Rat |
|---|---|---|---|---|---|---|---|
| $CH_3-C(SCH_3)=NOC(O)N(CH_3)(S-S-C(CH_3)_3)$ | 67–69 | A | C | A | A | A | 143 |
| $CH_3-C(S-CH(CH_3)_2)=NOC(O)N(CH_3)(S-S-C(CH_3)_3)$ | (oil) | A | A | A | A | A | 30.8 |
| $CH_3-C(SCH_3)=NOC(O)N(CH_3)(S-S-CH_3)$ | 56–57 | A | B | A | A | A | — |
| $CH_3-C(SCH_3)=NOC(O)N(CH_3)(S-S-C_8H_{17})$ | (oil) | A | A | A | A | A | — |

TABLE I-continued

BIOLICAL DATA

| Structure | m.p. °C | Aphid | Mite | Army-worm | Beetle | Fly | Rat |
|---|---|---|---|---|---|---|---|
| $CH_3-C(=NOC(=O)N(CH_3)(S-S-C(CH_3)_3))-SCH_2CH_2CN$ | 90-92 | A | A | A | A | A | 10 |
| $CH_3-SC(CH_3)_2-CH=NOC(=O)N(CH_3)(S-S-C(CH_3)_3)$ | (oil) | A | A | B | A | A | — |
| $CH_3-C(=NOC(=O)N(CH_3)(S-S-C_6H_4-C(CH_3)_3))-SCH_3$ | (oil) | A | B | A | A | A | — |

At higher dosage rates all of the above compositions may be expected to exhibit some activity against the various test species, however the data presented in Table I above clearly indicates a rather high degree of selectivity for some compositions and a broad spectrum of activity for others.

It will be understood that the insect species employed in the above tests are merely representative of a wide variety of pests that can be controlled by use of my compounds. These compounds demonstrate systemic as well as contact toxicity against insects and mites.

It should be noted that in addition to their insecticidal and miticidal activity, noteworthy nematocidal activity was also displayed by our compounds.

Comparison tests were conducted to assess the biological and chemical properties of certain representative species of the claimed invention in relation to methomyl, a corresponding N-methyl carbamate composition. The test procedures described above were employed in these experiments in order to determine the $LD_{50}$ (number of parts per million of active ingredients required to achieve fifty percent mortality of the insects tested) for each of the compositions tested. The results of these experiments are set forth in Table II below.

be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash if off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well

TABLE II
COMPARATIVE BIOLOGICAL ACTIVITY $$CH_3-C(X)=NOC(=O)N(CH_3)(R)$$

| Compound | R | X | Aphid | Mite | Army-worm | Beetle | Fly | Rat |
|---|---|---|---|---|---|---|---|---|
| Methomyl | H | —SCH$_3$ | 4 | >500 | 11 | 70 | 4 | 48 |
| Example II | —S—S—C(CH$_3$)$_3$ | —SCH$_3$ | 1.3 | >500 | 6 | 40 | 4 | 143 |
| Example III | —S—S—C(CH$_3$)$_3$ | —SCH(CH$_3$)$_2$ | 9 | 125 | 35 | 31 | 42 | 30.8 |

The compounds contemplated in this invention may be applied as insecticides, miticides and namatocides according to methods known to those skilled in the art. Pesticidal compositions containing the compounds as the active toxicant will usually comprise a carrier and-/or diluent, either liquid or solid.

Suitable liquid diluents or carriers include water, petroleum distillates, or other liquid carriers with or without surface active agents. Liquid concentrates may as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

What is claimed is:

1. A pesticide composition comprising an acceptable carrier and an insecticidally or miticidally effective amount of a compound of the formula:

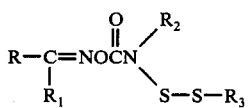

wherein:
R is carbamoyl, lower alkyl, alkylthio or lower alkyl substituted with one or more lower alkoxy, lower alkylthio, lower alkylsulfinyl, lower alkylsulfonyl, phenylthio, phenylsulfinyl, phenylsulfonyl, lower phenylalkylthio, lower phenylalkylsulfinyl, lower phenylalkylsulfonyl, lower alkylcarbamoyl, di-lower alkylcarbamoyl or $R_4CON(R_5)$— groups all of which groups may be further substituted with one or more chloro, bromo, fluoro, nitro, cyano or amido substituents and the phenyl moieties of said groups may be still further substituted with one or more lower alkyl or lower alkoxy groups;

$R_1$ is hydrogen, chloro, bromo, fluoro, cyano or a lower alkyl group having from 1 to 4 carbon atoms or a lower alkylthio, lower alkoxy, lower carboalkoxyalkylthio or lower alkylthioalkyl group in which any alkyl moiety may be substituted with one or more chloro, bromo, fluoro, cyano amido or nitro substituents;

$R_2$ is lower alkyl or lower alkyl substituted with one or more chloro, bromo, fluoro, nitro or cyano substituents or phenyl or lower phenyl alkyl, either unsubstituted or substituted with one or more chloro, bromo, fluoro, nitro, cyano, lower alkyl or lower alkoxy substituents;

$R_3$ is alkyl, alkenyl, cycloalkyl, bicycloalkyl, cycloalkenyl, bicycloalkenyl or phenyl or lower phenylalkyl either unsubstituted or substituted with one or more chloro, bromo, fluoro, nitro, cyano, lower alkyl, lower alkoxy or lower haloalkyl substituents;

$R_4$ and $R_5$ are individually hydrogen or lower alkyl.

2. A pesticide composition comprising an acceptable carrier and an insecticidally or miticidally effective amount of a compound of the formula:

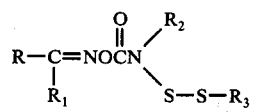

wherein:
R is:
(a) lower alkyl;
(b) lower alkylthio; or
(c) lower alkyl substituted with one or more lower alkoxy, lower alkylthio, lower alkylsulfinyl, lower alkylsulfonyl, phenylthio, phenylsulfinyl, phenylsulfonyl, lower phenylalkylthio, lower phenylalkylsulfinyl or lower phenylalkylsulfonyl;
wherein: the alkyl moieties of (a), (b), and (c) may be substituted with one or more chloro, bromo, fluoro, nitro, cyano, or amido substituents and the phenyl moieties of (c) may be substituted with one or more chloro, bromo, fluoro, nitro, cyano, amido, lower alkyl or lower alkoxy substituents $R_1$ is:
(a) hydrogen, chlorine, bromine, fluorine, cyano or
(b) lower alkyl having from 1 to 4 carbon atoms, lower alkylthio, lower alkoxy, lower carbaalkoxyalkylthio or lower alkylthioalkyl;
wherein the alkyl moieties of (b) may be substituted with one or more chloro, bromo, fluoro, cyano, amido or nitro substituents;

$R_2$ is:
(a) lower alkyl
(b) lower alkyl substituted with one or more chloro, bromo, fluoro, nitro, or cyano substituents
(c) phenyl or lower phenylalkyl
(d) phenyl or lower phenylalkyl each substituted with one or more chloro, bromo, fluoro, nitro, cyano, lower alkyl or lower alkoxy substituents $R_3$ is alkyl, alkenyl, cycloalkyl, bicycloalkyl, cycloalkenyl, bicycloalkenyl or phenyl or lower phenylalkyl either substituted or substituted with one or more chloro, bromo, fluoro, nitro, cyano, lower alkyl, lower alkoxy or lower haloalkyl substituents.

3. A pesticide composition in accordance with claim 2 in which the combined total number of aliphatic carbon atoms in substituents R, $R_1$ and $R_2$ does not exceed 10.

4. A pesticide composition in accordance with claim 2 in which $R_3$ is alkyl.

5. A pesticide composition in accordance with claim 2 in which $R_2$ is lower alkyl.

6. A pesticide composition in accordance with claim 2 in which $R_2$ is methyl.

7. A pesticide composition in accordance with claim 2 in which R is lower alkylthio.

8. A pesticide composition in accordance with claim 2 in which R is lower alkyl.

9. A pesticide composition in accordance with claim 2 in which $R_1$ is lower alkyl.

10. A pesticide composition in accordance with claim 2 in which $R_1$ is substituted lower alkyl.

11. A pesticide composition in accordance with claim 2 in which $R_1$ is lower alkylthio.

12. A pesticide composition in accordance with claim 2 in which R, $R_2$ and $R_3$ are lower alkyl and $R_1$ is lower alkylthio.

13. A pesticide composition in accordance with claim 2 in which R, $R_2$ and $R_3$ are lower alkyl and $R_1$ is substituted lower alkylthio.

14. A pesticide composition in accordance with claim 2 wherein said compound is methylthioacetaldehyde-O-[N-methyl-N-2(2-methylpropanethiosulfenyl)-carbamoyl]oxime.

15. A pesticide composition in accordance with claim 2 wherein said compound is 1-isopropylthioacetaldehyde-O-[N-methyl-N-2(2-methylpropanethiosulfenyl)-carbamoyl]oxime.

16. A pesticide composition in accordance with claim 2 wherein said compound is methylthioacetaldehyde-O-(N-methyl-N-methylthiosulfenylcarbamoyl)oxime.

17. A pesticide composition in accordance with claim 2 wherein said compound is methylthioacetaldehyde-O-(N-methyl-N-octylthiosulfenylcarbamoyl)oxime.

18. A pesticide composition in accordance with claim 2 wherein said compound is 2cyanoethylthioacetaldehyde-O-[N-methyl-N-2(2-methylpropanethiosulfenyl)-carbamoyl]oxime.

19. A method of controlling insects and mites which comprises subjecting them to a lethal amount of a compound of the formula:

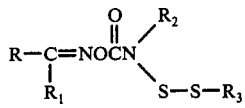

wherein:
R is carbamoyl, lower alkyl, lower alkylthio or lower alkyl substituted with one or more lower alkoxy, lower alkylthio, lower alkylsulfinyl, lower alkylsulfonyl, phenylthio, phenylsulfinyl, phenylsulfonyl, lower phenylalkylthio, lower phenylalkylsulfinyl, lower phenylalkylsulfonyl, lower alkylcarbamoyl, dilower alkylcarbamoyl or $R_4CON(R_5)$—groups all of which groups may be further substituted with one or more chloro, bromo, fluoro, nitro, cyano or amido substituents and the phenyl moieties of said groups may be still further substituted with one or more lower alkyl or lower alkoxy groups;

$R_1$ is hydrogen, chloro, bromo, fluoro, cyano or a lower alkyl group having from 1 to 4 carbon atoms or a lower alkylthio, lower alkoxy, lower carboalkoxyalkylthio or lower alkylthioalkyl group in which any alkyl moiety may be substituted with one or more chloro, bromo, fluoro, cyano, amido or nitro substituents;

$R_2$ is lower alkyl or lower alkyl substituted with one or more chloro, bromo, fluoro, nitro or cyano substituents or phenyl or lower phenyl alkyl, either unsubstituted or substituted with one or more chloro, bromo, fluoro, nitro, cyano, lower alkyl or lower alkoxy substituents;

$R_3$ is alkyl, alkenyl, cycloalkyl, bicycloalkyl, cycloalkenyl, bicycloalkenyl or phenyl or lower phenylalkyl either unsubstituted or substituted with one or more chloro, bromo, fluoro, nitro, cyano, lower alkyl, lower alkoxy or lower haloalkyl substituents;

$R_4$ and $R_5$ are individually hydrogen or lower alkyl.

20. A method of controlling insects and mites which comprises subjecting them to a lethal amount of a compound of the formula:

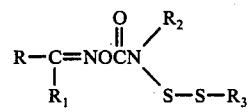

wherein:
R is :
(a) lower alkyl;
(b) lower alkylthio; or
(c) lower alkylsubstituted with one or more lower alkoxy, lower alkylthio, lower alkylsulfinyl, lower alkylsulfonyl, phenylthio, phenylsulfinyl, phenylsulfonyl, lower phenylalkylthio, lower phenylalkylsulfinyl or lower phenylalkylsulfonyl;

wherein: the alkyl moieties of (a), (b) and (c) may be substituted with one or more chloro, bromo, fluoro, nitro, cyano, or amido substituents and the phenyl moieties of (c) may be substituted with one or more chloro, bromo, fluoro, nitro, cyano, amido, lower alkyl or lower alkoxy substituents;

$R_1$ is:
(a) hydrogen, chlorine, bromine, fluorine, cyano, or
(b) lower alkyl having from 1 to 4 carbon atoms, lower alkylthio, lower alkoxy, lower carboalkoxyalkylthio or lower alkylthioalkyl;

wherein the alkyl moieties of (b) may be substituted with one or more chloro, bromo, fluoro, cyano, amido or nitro substituents;

$R_2$ is:
(a) lower alkyl
(b) lower alkyl substituted with one or more chloro, bromo, fluoro, nitro, or cyano substituents
(c) phenyl or lower phenylalkyl
(d) phenyl or lower phenylalkyl each substituted with one or more chloro, bromo, fluoro, nitro, cyano, lower alkyl or lower alkoxy substituents;

$R_3$ is alkyl, alkenyl, cycloalkyl, bicycloalkyl, cycloalkenyl, bicycloalkenyl or phenyl or lower phenylalkyl either unsubstituted or substituted with one or more chloro, bromo, fluoro, nitro, cyano, lower alkyl, lower alkoxy or lower haloalkyl substituents.

21. A method in accordance with claim 20 in which the combined total number of aliphatic carbon atoms in substituents R, $R_1$ and $R_2$ does not exceed 10.

22. A method in accordance with claim 20 in which $R_3$ is alkyl.

23. A method in accordance with claim 20 in which $R_2$ is lower alkyl.

24. A method in accordance with claim 20 in which $R_2$ is methyl.

25. A method in accordance with claim 20 in which R is lower alkylthio.

26. A method in accordance with claim 20 in which R is lower alkyl.

27. A method in accordance with claim 20 in which $R_1$ is lower alkyl.

28. A method in accordance with claim 20 in which $R_1$ is substituted lower alkyl.

29. A method in accordance with claim 20 in which $R_1$ is lower alkylthio.

30. A method in accordance with claim 20 in which R, $R_2$ and $R_3$ are lower alkyl and $R_1$ is lower alkylthio.

31. A method in accordance with claim 20 in which R, $R_2$ and $R_3$ are lower alkyl and $R_1$ is substituted lower alkylthio.

32. A method in accordance with claim 20 wherein said compound is methylthioacetaldehyde-O-[N-methyl-N-2(2-methylpropanethiosulfenyl)-carbamoyl]oxime.

33. A method in accordance with claim 20 wherein said compound is 1-isopropylthioacetaldehyde-O-[N-methyl-N-2(2-methylpropanethiosulfenyl)carbamoyl]oxime.

34. A method in accordance with claim 20 wherein said compound is methylthioacetaldehyde-O-(N-methyl-N-methylthiosulfenylcarbamoyl)oxime.

35. A method in accordance with claim 20 wherein said compound is methylthioacetaldehyde-O-(N-methyl-N-octylthiosulfenylcarbamoyl)oxime.

36. A method in accordance with claim 20 wherein said compound is 2-cyanoethylthioacetaldehyde-O-[N-methyl-N-2(2-methylpropanethiosulfenyl)carbamoyl]oxime.

* * * * *

UNITED STATES PATENT OFFICE
CERTIFICATE OF CORRECTION

Patent No. 4,080,469      Dated March 21, 1978

Inventor(s) T.D.J. D'Silva

It is certified that error appears in the above-identified patent and that said Letters Patent are hereby corrected as shown below:

Column 5, line 21 "pentanetriosulfenylcarbamoyl]oxime" should read "pentanethiosulfenylcarbamoyl]oxime".

Column 6, line 3 "thier" should read "their".

Column 12, line 27 "carbaalk-" should read "carboalk-".

Signed and Sealed this

Eighth Day of August 1978

[SEAL]

Attest:

RUTH C. MASON
Attesting Officer

DONALD W. BANNER
Commissioner of Patents and Trademarks